(12) United States Patent
Abell et al.

(10) Patent No.: US 8,828,210 B2
(45) Date of Patent: Sep. 9, 2014

(54) MICROFLUIDIC SYSTEMS

(75) Inventors: Chris Abell, Cambridgeshire (GB);
Wilhelm T. S. Huck, Cambridgeshire (GB); Daniel Bratton, Cambridgeshire (GB); Graeme Whyte, Cambridgeshire (GB); Luis M. Fidalgo, Cambridgeshire (GB)

(73) Assignee: Cambridge Enterprise Limited, Cambridge (GB)

( * ) Notice: Subject to any disclaimer, the term of this patent is extended or adjusted under 35 U.S.C. 154(b) by 1146 days.

(21) Appl. No.: 12/738,268

(22) PCT Filed: Oct. 16, 2008

(86) PCT No.: PCT/GB2008/050944
§ 371 (c)(1),
(2), (4) Date: Jul. 13, 2010

(87) PCT Pub. No.: WO2009/050512
PCT Pub. Date: Apr. 23, 2009

(65) Prior Publication Data
US 2012/0091004 A1    Apr. 19, 2012

(30) Foreign Application Priority Data
Oct. 16, 2007   (GB) .................... 0720202.1

(51) Int. Cl.
*B01J 19/08* (2006.01)
*B01D 17/06* (2006.01)
*B01J 19/00* (2006.01)
B01L 3/00 (2006.01)
G01N 35/00 (2006.01)

(52) U.S. Cl.
CPC ...... *B01J 19/0093* (2013.01); *B01J 2219/0097* (2013.01); *B01L 3/502761* (2013.01); *B01L 3/502784* (2013.01); *B01J 2219/00783* (2013.01); *B01J 2219/00576* (2013.01); *B01J 2219/00831* (2013.01); *B01J 2219/0086* (2013.01); *G01N 2035/00158* (2013.01); *B01J 2219/00833* (2013.01); *B01L 2400/043* (2013.01); *B01J 2219/00891* (2013.01); *B01L 2400/0415* (2013.01); *B01J 2219/00599* (2013.01); *B01J 2219/00853* (2013.01); *B01L 2300/0867* (2013.01)
USPC .......... 204/556; 204/557; 204/664; 210/222; 366/142; 366/341

(58) Field of Classification Search
USPC ................. 204/556, 557, 664; 210/695, 222; 366/348, 142, 341
See application file for complete search history.

(56) References Cited

U.S. PATENT DOCUMENTS

| | | | |
|---|---|---|---|
| 3,710,933 A | 1/1973 | Fulwyler et al. | |
| 6,140,048 A | 10/2000 | Muller et al. | |
| 2001/0048637 A1 | 12/2001 | Weigl et al. | |
| 2004/0005628 A1 | 1/2004 | Foster | |
| 2004/0115838 A1 | 6/2004 | Quake et al. | |
| 2004/0211659 A1 | 10/2004 | Velev | |
| 2004/0219078 A1 | 11/2004 | Kitamori et al. | |
| 2004/0233424 A1 | 11/2004 | Lee et al. | |
| 2005/0128479 A1 | 6/2005 | Gilbert et al. | |
| 2006/0280029 A1 | 12/2006 | Garsteck et al. | |
| 2012/0091004 A1 | 4/2012 | Abell et al. | |

FOREIGN PATENT DOCUMENTS

| | | |
|---|---|---|
| DE | 102010 012 580 A1 | 9/2011 |
| EP | 1 380 337 A2 | 4/2004 |
| EP | 2 047 910 B1 | 1/2012 |
| WO | WO 96/12541 | 5/1996 |
| WO | WO-99/64840 A1 | 12/1999 |
| WO | WO-02/23163 A1 | 3/2002 |
| WO | WO 2004/071638 A2 | 8/2004 |
| WO | WO-2005/021151 A1 | 3/2005 |
| WO | WO-2007/081387 A1 | 7/2007 |
| WO | WO-2008/130871 A2 | 10/2008 |
| WO | WO-2011/005776 A1 | 1/2011 |
| WO | WO-2011/129956 A1 | 10/2011 |

OTHER PUBLICATIONS

Copy of United Kingdom Search Report corresponding to GB0720202.1, dated Feb. 15, 2008, 1 page.
Copy of International Search Report corresponding to PCT/GB2008/050944, dated Dec. 28, 2009, 3 pages.
Ahn et al., "Dielectrophoretic Manipulation of Drops for High-Speed Microfluidic Sorting Devices," Applied Physics Letters, 88:024104 (3 pages) (2006).
Ahn et al., "Electrocoalescence of Drops Synchronized by Size-Dependent Flow in Microfluidic Channels," Applied Physics Letters 88:264105 (3 pages) (2006).
Anna et al., "Formation of Dispersions Using 'Flow Focusing' in Microchannels," Applied Physics Letters, 82:364 (2003).
Bibette et al., "Emulsions: Basic Principles," Reports on Progress in Physics—IOP Science, 62:969-1033 (1999).
Horiba, "Fluorolog-3, How to Build a Spectrofluorometer," Horiba Jobin Yvon (2005).
International Preliminary Report on Patentability for corresponding Application No. PCT/GB2008/050944, dated Apr. 20, 2010.
Kralj et al., "Surfactant-Enhanced Liquid-Liquid Extraction in Microfluidic Channels With Inline Electric-Field Enhanced Coalescence," Lab Chip, 5:531-535 (2005).
Siegel et al., "Microsolidics: Fabrication of Three-Dimensional Metallic Microstructures in Poly(dimethylsiloxane)," Advanced Materials, 19:727-733 (2007).
Wehry, "Molecular Fluorescence and Phosphorescence Spectrometry," Handbook of Instrumental Techniques for Analytical Chemistry, 507-539 (1997).

*Primary Examiner* — J. Christopher Ball
(74) *Attorney, Agent, or Firm* — Foley & Lardner LLP

(57) ABSTRACT

This invention relates to microfluidic systems and more particularly to methods and apparatus for accessing the contents of micro droplets (114) in an emulsion stream. A method of accessing the contents of a droplet (114) of an emulsion in a microfluidic system, the method comprising: flowing the emulsion alongside a continuous, non-emulsive stream of second fluid (118) to provide an interface (120) between said emulsion and said stream of second fluid (118); and in embodiments applying one or both of an electric (112a, 112b) and magnetic field across said interface (120) to alter a trajectory of a said droplet (114) of said emulsion to cause said droplet to coalesce with said stream of second fluid (118); and accessing said contents of said droplet (114) in said second stream (118).

24 Claims, 6 Drawing Sheets

Figure 1b,c

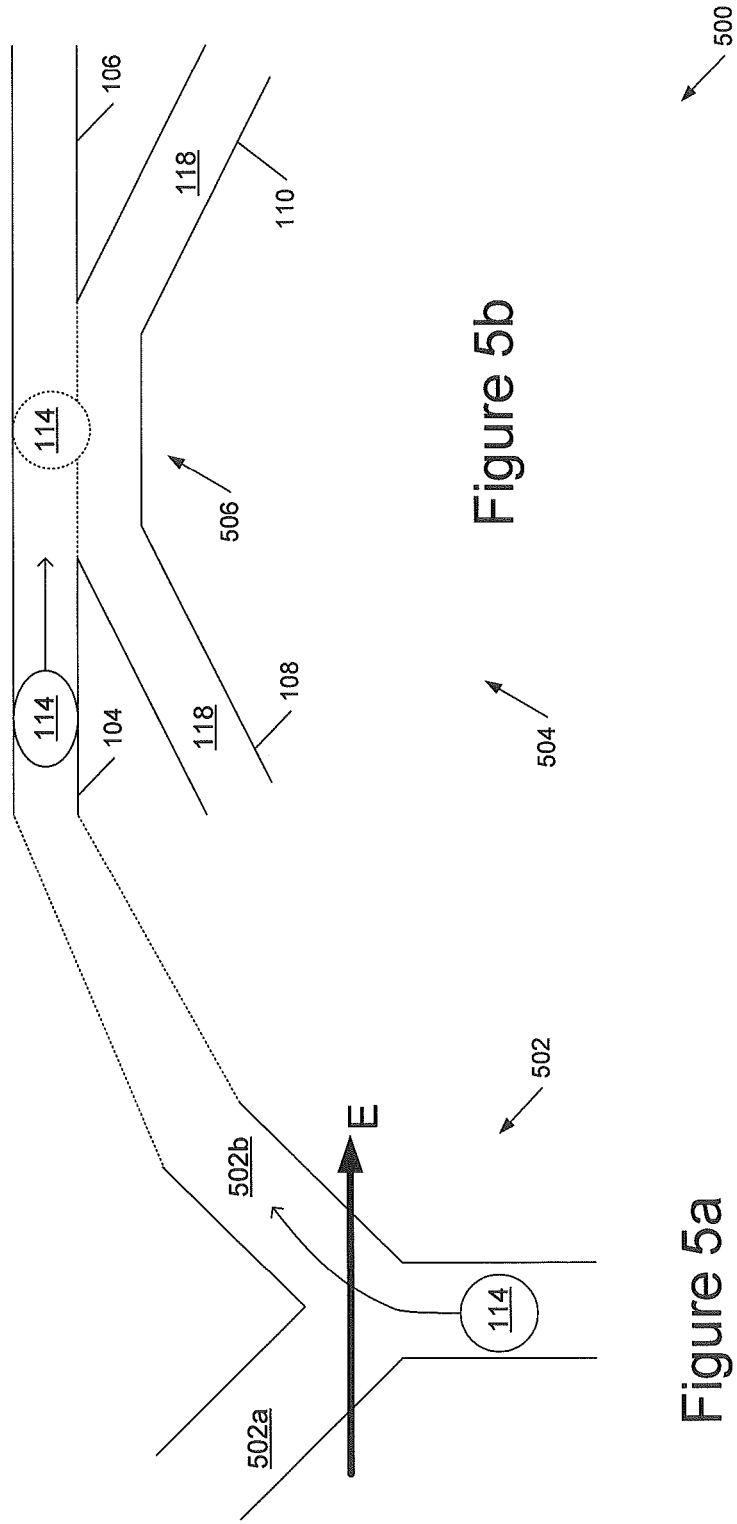

MICROFLUIDIC SYSTEMS

CROSS-REFERENCE TO RELATED APPLICATIONS

This application is a National Stage application of PCT/GB2008/050944, filed Oct. 16, 2008, which claims the priority of Great Britain Patent Application No. 0720202.1, filed Oct. 16, 2007. The foregoing applications are incorporated by reference herein in their entirety.

SUMMARY OF THE INVENTION

This invention relates to microfluidic systems and more particularly to methods and apparatus for accessing the contents of micro droplets in an emulsion stream.

BACKGROUND TO THE INVENTION

Micro droplets show great promise as a new high-throughput technology in chemistry, biochemistry and molecular biology. Micro droplets can be generated at rates in excess of several thousands per second and accurately formulated using minute amounts of small molecules, DNA, proteins or cells. Furthermore, integrated active elements can be used to control individual droplets. With technology for creating, dividing, fusing, interrogating and even sorting micro droplets already developed, one of the main problems to be resolved is how to access their contents.

Droplets are naturally self-contained microreactors that prevent sample loss, diffusion and cross-contamination, general issues that afflict traditional microfluidics. However, the isolated nature of droplets prevents physical access of their contents on-chip. Even though this does not represent a problem for many of the applications that have already been demonstrated, it limits the integration of microdroplets with other platforms. Analytical techniques such as mass spectrometry, capillary electrophoresis or liquid chromatography have been successfully integrated with continuous flow micro fluidic devices, but their integration with microdroplets remains hindered.

Background prior art relating to microdroplets can be found in: K. Ahn, J. Agresti, H. Chong, M. Marquez, D. A. Weitz, *Applied Physics Letters* 2006, 88, 264105; L. M. Fidalgo, C. Abell, W. T. S. Huck, *Lab Chip* 2007, 7, 948; Y.-C. Tan, J. S. Fisher, A. I. Lee, V. Cristini, A. P. Lee, *Lab Chip* 2004, 4, 292; P. S. Dittrich, M. Jahnz, P. Schwille, *ChemBioChem* 2005, 6, 811; K. Ahn, C. Kerbage, T. P. Hunt, R. M. Westervelt, D. R. Link, D. A. Weitz, *Appl. Phys. Lett.* 2006, 88, 024104; P. S. Dittrich, K. Tachikawa, A. Manz, *Anal. Chem.* 2006, 78, 3887; J. Bibette, F. L. Calderon, P. Poulin, *Rep. Prog. Phys.* 1999, 62, 969; J. S. Eow, M. Ghadiri, A. O. Sharif, T. J. Williams, *Chemical Engineering Journal* 2001, 84, 173; P. Atten, *Journal of Electrostatics* 1993, 30, 259; J. G. Kralj, M. A. Schmidt, K. F. Jensen, *Lab Chip* 2005, 5, 531; C. Priest, S. Herminghaus, R. Seemann, *Appl. Phys. Lett.* 2006, 89, 134101; "Phase separation of segmented flow by the photocatalytic wettability patterning and tuning of microchannel surface", Go Takei, Arata Aota, Akihide Hibara, Takehiko Kitamori and Haeng-Boo Kim, Eleventh International Conference on Miniaturized systems for Chemistry and Life Sciences, 7-11 Oct. 2007, Paris, France; and also WO2005/021151, WO2007/081387, US2001/0048637, US2004/0219078, EP1380337, and US2006/0280029.

There therefore remains a need for improved techniques for accessing the contents of microdroplets.

SUMMARY OF THE INVENTION

According to a first aspect of the invention is therefore provided a method of accessing the contents of a droplet of an emulsion in a microfluidic system, the method comprising: flowing the emulsion alongside a continuous, non-emulsive stream of second fluid to provide an interface between said emulsion and said stream of second fluid; and applying one or both of an electric and magnetic field across said interface to alter a trajectory of a said droplet of said emulsion to cause said droplet to coalesce with said stream of second fluid; and accessing said contents of said droplet in said second stream.

Embodiments of the method enable the contents of microdroplets to be readily extracted on demand, discarding the carrier fluid, and converting them into a continuous stream. This in turn enables microfluidic functionality to be combined with the advantages provided by microdroplets.

In embodiments the emulsion comprises a dispersed phase of water in oil and the second fluid comprises an aqueous fluid; potentially double emulsions may be employed. The applied field may comprise an electric field, a magnetic field, or a combination of the two which includes, for example, laser light (not limited to visible wavelength). This de-stabilises the interface between the emulsion and the second fluid and thus enables the drop to coalesce with the second fluid, thus enabling the contents of the droplet to be analysed or otherwise further processed using microfluidic techniques. Embodiments of the method are so effective that there is substantially no oil in the continuous stream of second fluid and the contents of the droplet are as if they had never been in the emulsion in the first place. As the skilled person would understand the presence of oil in the output stream would make many microfluidic analytical techniques impractical or impossible.

In some preferred implementations of the method one or more properties of the droplets are detected and the electric and/or magnetic fields are applied to selectively merge the droplet with the second stream. For example a fluorescence of the droplet may be detected to determine the presence or absence of a substance within the droplet. To facilitate selection the field may be pulsed and the duration of a pulse adjusted so that only a single droplet is present, for example between a pair of electrodes or in a laser beam, during a pulse. The pulse may comprise a pulse above or below a base line level of the field.

In embodiments the applied field comprises an electric field applied with a pair of electrodes and disposed laterally either side of the stream of emulsion and the stream of second (aqueous) fluid. In embodiments the electric field is substantially perpendicular to laminar flows of the two streams. In embodiments a droplet flows past the interface between the two streams at a distance of greater than 1 micrometer from the interface. Preferably therefore in embodiments the electric field has a value at the interface of at least $10^6$ volts per meter, preferably of the order of $10^7$ volts per meter.

There is a particular need for high-throughput systems, that is systems capable of processing droplets at rates faster than 1 KHz, 5 KHz or, preferably, 10 KHz droplets per second. This is useful, for example, when screening a large library of items. At high throughputs the above-described techniques can be difficult to apply because droplets are closely spaced in the stream of emulsion. The inventors have found, however, that the above described techniques need not rely upon the application of an electric and/or magnetic field to cause the droplet to coalesce with the second stream of fluid; instead this may be performed using the geometry of the microfluidic system, but configuring the geometry so as to cause a droplet to collide with the interface between the emulsion and the stream of second fluid. Again this effectively de-stabilises this interface.

According to another aspect of the invention there is therefore provided a method of accessing the contents of a droplet of an emulsion in a microfluidic system, the method comprising: flowing the emulsion alongside a continuous, non-emulsive stream of second fluid such that said droplet coalesces with said stream of second fluid; and accessing said contents of said droplet in said second stream.

In embodiments the geometry of microfluidic channels carrying the stream of emulsion and the stream of second fluid is arranged so that there is a region, for example a chamber, in which a droplet collides with the interface between these two streams, enabling the droplet to coalesce with the second stream. One way in which this may be achieved is by confining a droplet within a micro fluidic channel so that the channel constrains the droplet into a shape different to that which, unconstrained, surface forces would cause it to adopt. This confined droplet is then allowed to expand into a chamber in which the interface is located so that a surface of the droplet is brought into contact with the interface, hence de-stabilising the interface and causing the droplet to coalesce with the second stream of fluid (here "expand" will be understood to be referring to expansion in one or more dimensions in which the droplet is constrained within the microfluidic channel, since the droplet volume per se remains unchanged).

In some preferred embodiments the method is implemented in a four-port chamber, with inlet and outlet ports for the stream of emulsion and inlet and outlet ports for the stream of second fluid.

A technique such as that described above enables screening to take place in two stages, a first stage in which a droplet is selectively directed into one of two or more microfluidic channels, for example responsive to a detected signal such as fluorescence. Down stream one (or more) of these channels is then directed to a region in which droplets of an emulsion stream in that channel coalesce with the stream of second fluid. The contents of the droplets selected upstream may be accessed via the stream of second fluid, for example for analysis by any of a range of micro fluidic techniques such as will be well known to those skilled in the art.

Thus in a still further aspect the invention provides a method of microfluidic screening the droplets of a flowing emulsion, the method comprising: flowing the emulsion alongside a continuous, non-emulsive stream of a second fluid to provide an interface between said emulsion and said stream of second fluid to cause said droplet to coalesce with said stream of second fluid; and detecting a property of said droplets of said flowing emulsion prior to said droplets flowing past said interface; and selectively incorporating the contents of said droplets of said flowing emulsion into a continuous microfluidic stream of said second fluid; and wherein the method further comprises selectively directing the trajectory of a said droplet responsive to said detecting to thereby selectively coalesce said droplets of said flowing emulsion with said second stream responsive to said detecting.

Techniques such as those described above facilitate the implementation of very high throughput combined micro-droplet-micro fluidic processing systems.

The skilled person would understand that in embodiments of the above-described techniques the contents of the droplet may comprise a very wide range of materials, but in some preferred embodiments the contents include at least one insoluble object such as a crystal or, more particularly, a solid support such as a bead or microsphere. In embodiments of the techniques each droplet contains no more than one such insoluble object; this facilitates processing and analysis.

One particularly advantageous process which is enabled by embodiments of the above-described techniques is use of the second stream to perform some active function in processing or analysis of the contents of the droplets. Thus a composition of the second fluid may be employed to perform a biological or chemical operation on the contents of a droplet, for example to quench a chemical reaction or to lyse a cell.

In a related aspect the invention provides a microfluidic device for accessing the contents of a droplet of an emulsion in a microfluidic system, the apparatus comprising: a flow cell, said flow cell having: a first microfluidic entry channel and first microfluidic exit channel for flowing said emulsion through said cell; a second microfluidic entry channel and second microfluidic exit channel for flowing a stream of second fluid through said cell, and wherein, in operation, an interface is formed in said cell between said emulsion and said stream of second fluid, and wherein said device further comprises a system to cause said droplet to coalesce with said stream of second fluid; whereby said contents of said droplet in said second stream are accessible from said second stream of fluid from said second microfluidic exit channel.

Preferably the system comprises means for applying an electric and/or magnetic field (which may include, for example, means for focussing a laser light on the interface). In embodiments a pair of electrodes is provided for applying a lateral electric field across the interface between the stream of emulsion and the stream of second fluid.

In a still further aspect the invention provides a microfluidic system comprising: an emulsion input to receive a stream of emulsion comprising a plurality of droplets of a dispersed phase of said emulsion in a continuous liquid phase; a second input to receive a continuous, non-emulsive stream of second fluid; a system for selectively merging a droplet into said continuous stream of second fluid responsive to a content of the said droplet; and a microfluidic output to provide said stream of second fluid including the contents of a said droplet to a microfluidic analytical device.

In embodiments of the system the output stream of second fluid is substantially free of any components of the continuous phase of the emulsion, at least as a dispersed phase that is in embodiments substantially free of oil. (In some embodiments a small amount of the continuous phase of the emulsion may be present as a further laminar flow alongside the stream of second fluid, but, if present, this is easily separated from the stream of second fluid). In embodiments the system includes the analytical device, optionally integrated on a common microfluidic platform with the droplet contents extraction system.

Preferably the system includes means for selectively coalescing droplets with the stream of second fluid, for example either by selectively directing a droplet onto the stream by an electric/magnetic field or by providing a system to selectively direct a droplet down one of a plurality of microchannels for later coalescing with the second stream.

Broadly speaking embodiments of a microfluidic system as described above, have a microfluidic channel with at least one dimension less than 1 mm, typically of order 10 μm to 500 μm. A microdroplet is generally less than 500 μm, 200 μm or 100 μm, for example in the range 20 μm to 100 μm, although microdroplets might be generated down to a dimension of order 1 μm (or even less). Generally speaking microfluidics are characterised by low Reynolds numbers, typically much less than one, this reflecting the relatively low importance of inertia compared with viscose and surface effects, and hence the substantially laminar flow that results.

Features of the above-described aspects and embodiments of the invention may be combined in any permutation.

BRIEF DESCRIPTION OF THE DRAWINGS

These and other aspects of the invention will now be further described, by way of example only, with reference to the accompanying figures in which:

FIGS. 1a to 1c show, respectively, a view from above of a microfluidic device for selective emulsion separation according to an embodiment of the invention, a micrograph illustrating the device in operation in the absence of a field and a micrograph illustrating the device in operation when a field is applied;

FIGS. 5a and 5b show, schematically, microfluidic screening apparatus with separate regions for selective emulsion separation and droplet-stream coalescence according a second embodiment of the invention.

DETAILED DESCRIPTION OF PREFERRED EMBODIMENTS

We will describe a technology that bridges the fields of microdroplets and continuous flow microfluidics by extracting on-chip the contents of microdroplets and incorporating them into a continuous stream. The extraction is achieved through electrocoalescence: droplets are forced to coalesce with an aqueous stream by applying an electric field across the channel The extraction is controlled through the voltage applied at microfabricated electrodes on each side of the channel and can be performed in a continuous or discrete fashion. The discrete collection of droplets can be triggered by an external electrical signal. Interestingly, this signal can be related to the contents of the droplets. As a proof of principle, we have implemented a fluorescence intensity-based detection system to control the collection of the droplets, resulting in a device capable of selectively incorporating the contents of droplets of interest to a continuous microfluidic stream.

We use flow-focusing to generate microdroplets (S. L. Anna, N. Bontoux, H. A. Stone, *Appl. Phys. Lett.* 2003, 82, 364). An aqueous stream is focused between two oil streams as they pass through a junction. Shear forces make the aqueous thread break up into monodisperse droplets. Droplet size and frequency are controlled by a combination of channel dimensions and flow rates. We use a mixture of flourous oil (FC-77) and 1H,1H,2H,2H-perfluorooctanol (70:30 by weight) as the carrier phase. The oil and aqueous flows at the flow-focusing device are adjusted to generate the desired droplet frequency, typically ranging from 10-250 Hz. The flow of a lateral aqueous phase is adjusted so an interface is held in the region between the electrodes but no overflow in either direction occurs.

Figure 1A:
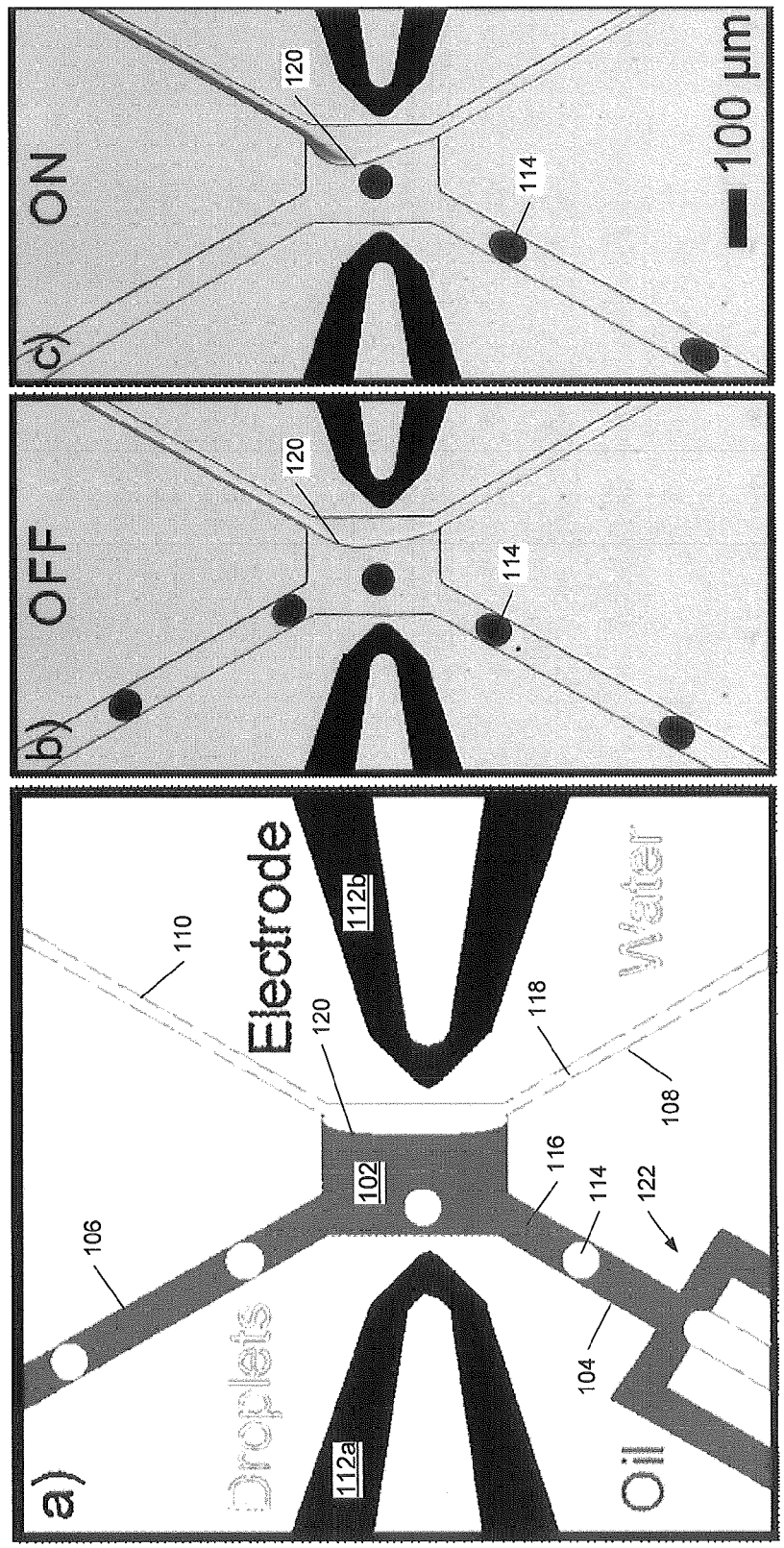

Referring now to FIG. 1a, this shows a microfluidic device 100 according to an embodiment of an aspect of the invention. The device comprises a chamber 102 with a first inlet 104 and first outlet 106 for a stream of emulsion and a second inlet 108 and second outlet 110 for an aqueous (water) stream. A pair of electrodes 112a, b are located to either side of chamber 102 to apply a lateral electric field to the flows within the chamber. FIG. 1a shows the device in operation illustrating droplets 114 of an aqueous solution being carried by an oil emulsion 116 through chamber 102 by channels 104, 106. At the same time a second stream of aqueous solution 118 is carried through chamber 102 by channels 108, 110, thus forming an interface 120 between the oil 116 and the aqueous solution 118 within chamber 102. In the illustrated example the droplets 114 are generated by a flow focussing device 122, but the skilled person will understand that many other techniques may also be employed to generate the emulsion, for example a microfluidic T-junction.

We used soft lithographic techniques to fabricate poly (dimethylsiloxane) (PDMS) microfluidic channels and oxygen plasma to seal the channels with PDMS coated glass slides (see, for example, Y. Wang, H. -H. La, M. Bachman, C. E. Sims, G. P. Li, N. L. Allbritton, *Anal. Chem.* 2005, 77, 7539). Solder electrodes were fabricated using microsolidics (see, for example, A. C. Siegel, D. A. Bruzewicz, D. B. Weibel, G. M. Whitesides, *Adv. Mater.* 2007, 19, 727). Extra channels for the electrodes were included in the mold used to fabricate the fluidic channels. After the plasma treatment, the devices were placed on a hot plate at 130° C. (solder melting point 60° C.). When the device temperature had equilibrated, we introduced solder rods in previously punched holes, filling the cavity completely with solder by capillarity. Before removing the device from the hotplate, while the sold was still liquid, we introduced copper wires in the solder channels to serve as electrical contacts. Our typical device presents 50 µm wide channels for droplet formation and a 20 µm wide channel for the lateral stream. The channel in the electrode area is 170 µm wide, with the electrodes 10 µm from the walls. Channels are 25 µm deep.

In operation droplets generated on-chip flow parallel to a stream of water between two electrodes. In the absence of an electric field, the droplets are not perturbed by the presence of the aqueous stream and follow the geometrically determined flow lines. FIGS. 1b and c show micrographs of such a device in operation. Droplets of a dye generated at the flow focussing device flow past the electrode region on the absence of a field (b) whereas they coalesce with the lateral stream when a field is applied (c). As a result the dye contained in the droplets is transferred from its discrete carriers into a continuous stream.

In FIG. 1b, in the absence of an electric field, droplets of a dye $(Fe(SCN)_x^{(3-x)})$ 67 mM) flow past the electrode region with out interacting with the aqueous stream. FIG. 1c shows the collection of droplet contents. In the presence of an electric field, droplets coalesce with the lateral aqueous stream as they enter the electrode region and the dye contained in them is transferred to the stream. In this example the droplet frequency was ~240 Hz; the applied voltage in FIG. 1c was 2.3 kV.

In general, coalescence occurs when two or more interfaces approach below a critical distance, in the order of hundreds of nanometers, for a sufficient length of time. The critical distance and time depend on the chemical nature of the system and its dimensions. Electrocoalesence follows the same general mechanism but is modified due to electric forces appearing at the interfaces. When a voltage difference is applied to the electrodes an electric field in the direction perpendicular to the flow is created. This field is capable of altering the trajectory of the droplets and of polarising the interfaces. Above a threshold voltage, these effects can induce coalescence between the droplets and the aqueous stream.

In our experiments, typical voltages required to induce 100% coalescence ranged from 1.5 to 3 kV. Coalescence starts to occur at approximately 70% of the voltage necessary for total coalescence. These values of applied voltage generate an electric field of $\sim 10^7$ V/m. This relatively large electric field may be partially due to a larger distance between the interfaces (on the order of micros instead of tenths to hundreds of nanometers) and the short time of contact due to their relative motion (usually coalescing droplets are not moving with respect to each other).

We frequently observed a decay in the percentage of coalescence after establishing an electric field. One possible technique to address this problem is the use of pulsed fields, which have increased coalescence efficiency in bulk. A very interesting feature of using pulsed fields in a microfluidic environment is the ability to address individual droplets, as this provides a tool to access the contents of a single droplet on demand.

The above described technique employs an electric field to de-stablise the interface 120 between the oil and water but in other embodiments a magnetic field may be employed to de-stabilise this interface and hence facilitate coalescence. In still further embodiments de-stabilisation of the interface may be performed by focussing a laser on the interface.

Figure 2:
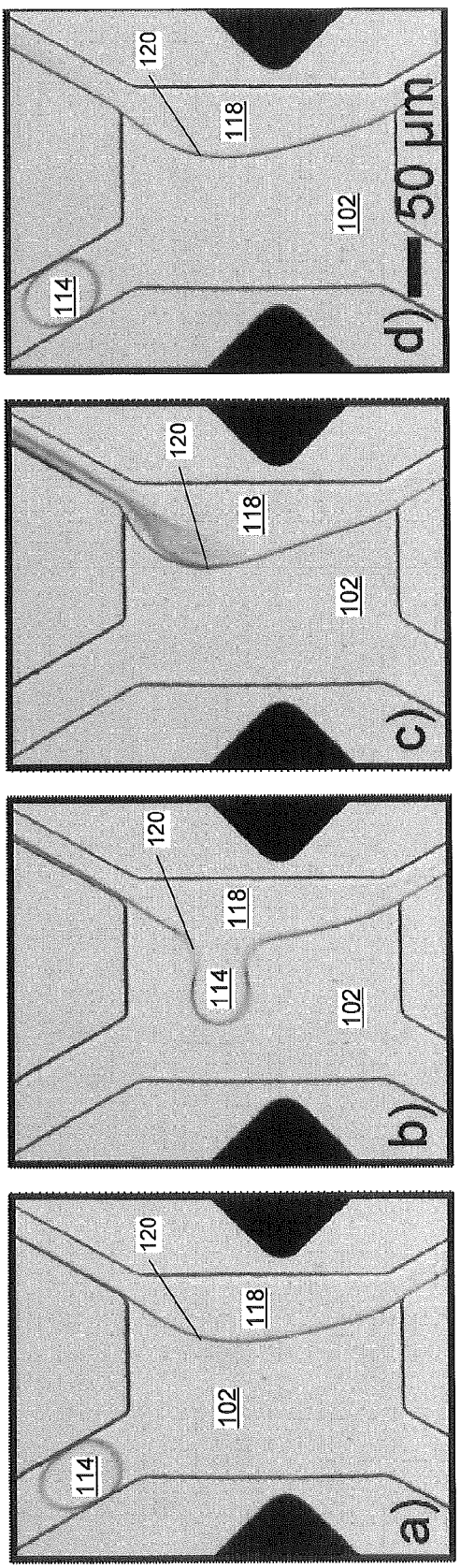
FIGS. 2a to 2d show a sequence of micrographs illustrating the extraction of the contents of an individual droplet.

FIG. 2 shows a sequence of micrographs where an individual droplet is selected from a stream. As shown in FIG. 2a, droplets flow past the electrodes when the applied potential (electric field) is insufficient for coalescence. When an additional square pulse is applied (FIG. 26), an individual droplet is selected and it is fused with its contents incorporated into the lateral aqueous stream. The applied voltage is then returned to its previous value before the droplet enters the electrode region and droplets then flow past again without coalescing. After the extraction, the contents of the droplet (in this example KSCN 0.8M) are incorporated into the aqueous lateral stream ($Fe(NO_3)_3$ 0.268M) and react with it, forming a coloured complex. To select an individual droplet it is important to ensure that only one droplet enters the region between the electrodes during the length of the pulse, therefore the pulse width and starting point must be carefully adjusted. In the illustrated example the droplet frequency was ~100 Hz, the pulse voltage 0.8 KV, the pulse width 10 ms and a baseline offset voltage of 2.5 KV was applied.

The pulses used to induce coalescence can be controlled by an external electrical signal. In order to demonstrate the potential of selective emulsion separation we chose to combine it with fluorescence intensity detection.

Figure 3:
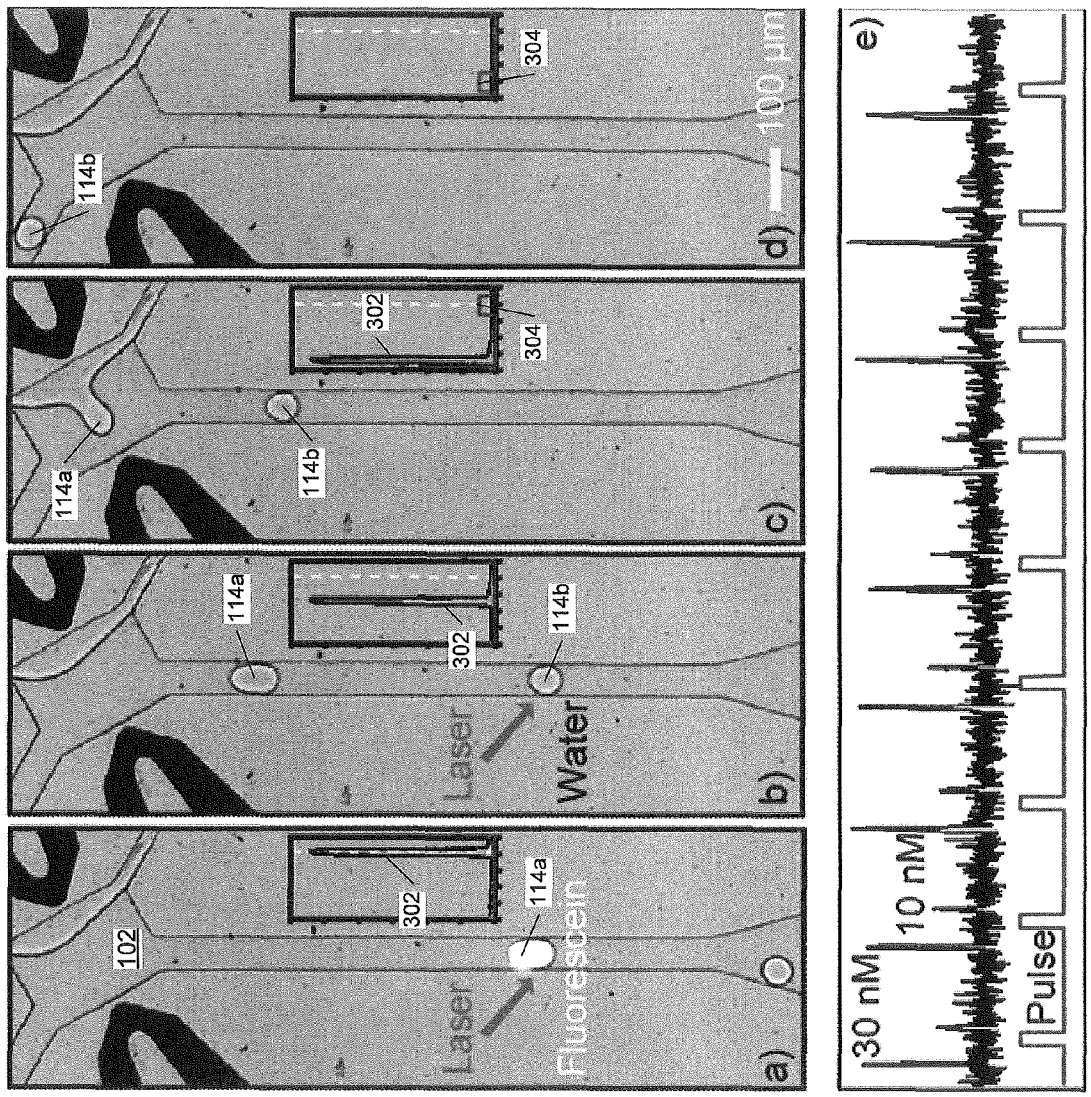
FIGS. 3a to 3f show, respectively a sequence of micrographs illustrating the selection and extraction of a fluorescent droplet of the device; a trace from a separate experiment illustrating the separation of droplets containing 30 nM fluorescein from droplets containing 10 nM fluorescein; and a schematic diagram of the microscope setup used.
Figure 3F:
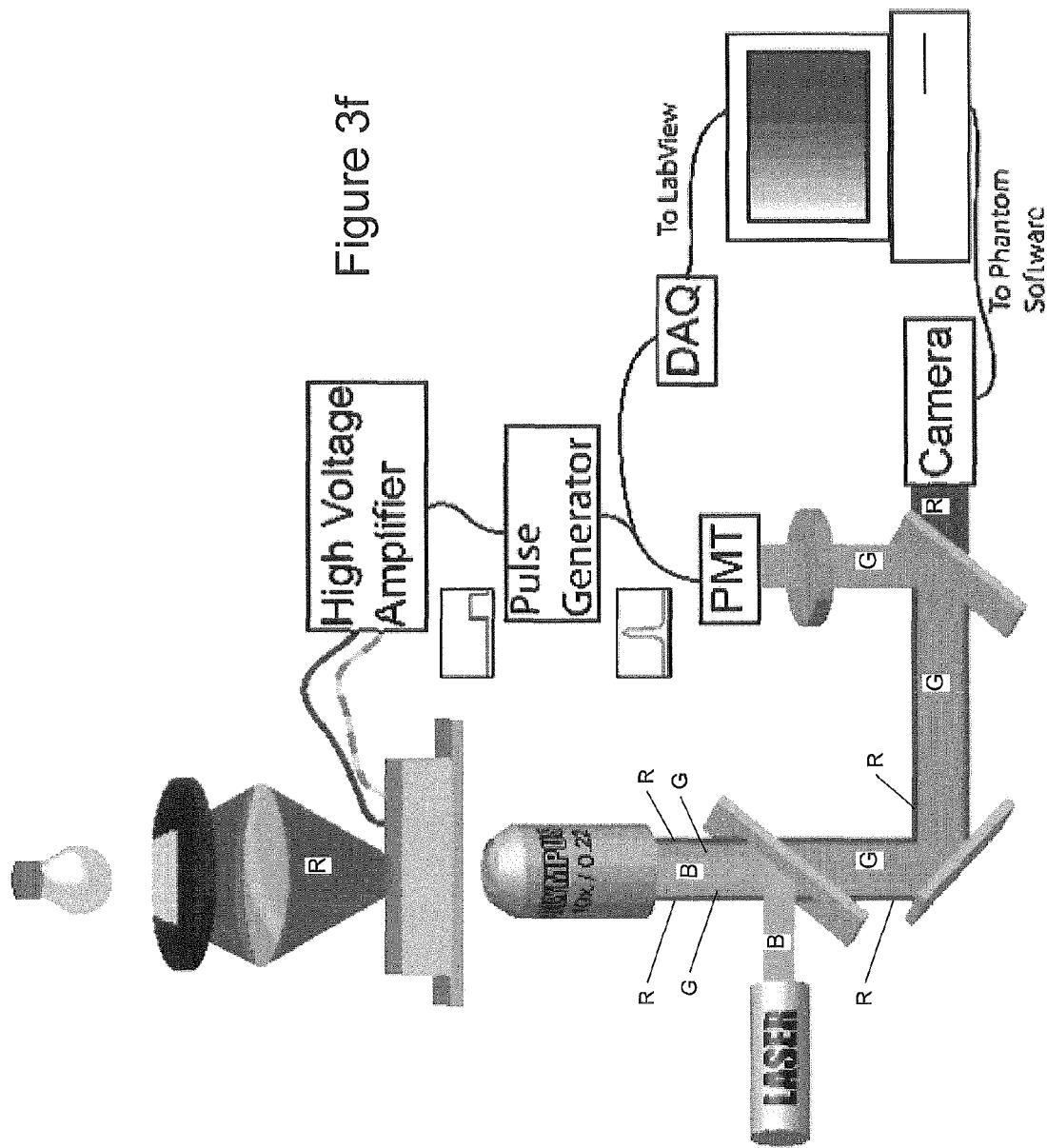

Using the level of fluorescence emitted by droplets to trigger the pulses we can discriminate them based on their contents. This discrimination can be used as the basis for selective emulsion separation in micro fluidic devices. FIG. 3f shows the setup used, inter alia, to induce electrocoalescence based on fluorescence intensity detection (R, G and B refer to red, green and blue light respectively in this example figure).

Referring to FIG. 3f, the setup is based around an Olympus IX70 inverted microscope. The illumination light for imaging the device is filtered and focussed onto the device. Transmission images are obtained using a CCD camera (Phantom v7.2, Phantom Cameras, USA). For FIGS. 1 and 2 the illumination light is filtered using a green bandpass (A52-535, Edmund Optics, UK) to increase contrast, while for FIGS. 3 and 4 (described below), a red longpass (A52-529, Edmund Optics, UK) is used to allow seperation of the illumination light and emission of the fluorescein. In FIG. 2 where no fluorescent detection is used, the dichroic mirrors and PMT were not present and triggering of the pulse generator was performed manually. To achieve fluorescent detection, a 20 mW, 488 nm DPSS laser was coupled to the microscope via a long-pass dichroic mirror (FF500-Di01, Semrock, USA) which reflects the laser light into the objective while allowing the green emission light to pass through to the detection. A red-green dichroic (A47-423long pass, Edmund Optics, UK) is used to separate the illumination and emitted light and a 520 nm bandpass filter is placed in front of the PMT to block non-fluorescein emission light. The output of the PMT is fed into the pulse generator and a DAQ card for recording. The generated pulses are amplified through a high-voltage amplifier connected to the device.

In operation the detector (photomultiplier tube, PMT) reads out a signal which is proportional to the fluorescence of the excited droplet. When the signal exceeds the threshold of the pulse generator trigger, a high voltage pulse is applied across the electrodes. The gain of the PMT can be adjusted to allow the triggering to take place at any level of fluorescence, with the signal-to-noise ratio determining the reliability. The use of a pulse generator allows the width and voltage of the pulse to be changed independently of the signal which triggers it.

FIGS. 3a to 3d show a sequence of micrographs where a fluorescent droplet is detected and fused while a non-fluorescent droplet flows past the electrodes undisturbed. Using a device comprising of two separate flow focusing devices we generated a stream of alternating fluorescent and non-fluorescent droplets. When the fluorescent droplets flow past the laser the emitted light is gathered by the detector whose signal triggers a pulse that induces coalescence. Non-fluorescent droplets do not trigger a pulse and therefore are not incorporated into the lateral stream. The laser detection point is arbitrarily chosen, and a time delay between the detection and the pulse is introduced to account for the distance the droplets have to cover between the laser and the electrodes.

In more detail, insets shows 10 ms of signal 302 from the detector and signal 304 from the pulse generator with the current frame position marked with a vertical dashed line. In FIG. 3a, a droplet 114a containing 12 mM fluorescein flows through the laser spot and emits fluorescent light which is detected by the PMT; in FIG. 3 b a water droplet 114b passes through the laser spot without fluorescing. In FIG. 3c, an electric pulse across the electrodes causes the droplet 114a containing fluorescein to merge with the lateral stream. In FIG. 3d the field is removed before the water droplet 114b passes between the electrodes so it flows past. FIG. 3c shows the trace from a separate experiment showing the signal from the PMT (upper) and pulse generator (lower) for a stream of droplets (frequency ~80 Hz) containing 30 nM and 10 nM fluorescein droplets, showing that only the droplets containing 30 nM fluorescein trigger the pulse generator (pulse details: voltage 0.5 kV, width 2.5 ms, delay 3.5 ms, offset voltage 1 kV).

These experiments demonstrate that: the duration of reactions can be accurately controlled (start time and flow rate i.e. elapsed time are well-defined), droplet formulation is carried out using microfluidic techniques, and the contents of the target droplets are extracted on-chip allowing further processing. For high-throughput screening, it is generally important to be able to select droplets containing low concentrations of fluorophores from an array of concentrations very similar to the target. To demonstrate the capability of this system for such studies we selected droplets containing 30 nM fluorescein from a stream that contained droplets of 30 and 10 nM concentrations. FIG. 3 (e) shows the trace of successful pulse triggering for droplets containing 30 nM fluorescein whereas droplets 10 nM in concentration do not trigger pulses. Analysis of a larger sequence of the trace (not shown) shows that all 30 nM and less than 1% of the 10 nM droplets were selected. The lower limit of fluorescein concentration for successful triggering in our experiments was 15 nM, beyond which the signal-to-noise ratio was too low to trigger the pulses reliably. The noise in our system was due to the illumination light used to capture the videos and ensure selection was taking place. If visual confirmation of the selection process was not required, the signal to noise should be substantially improved.

Solid supported chemistry and biochemistry plays an important role in biotechnology, drug discovery and combinatorial chemistry. Our techniques allow combining solid supported chemistry such as microspheres/beads and microdroplets in a microfluidic environment, in particular for higher-throughput technologies. We used selective emulsion separation to detect and extract fluorescent beads encapsulated in microdroplets and incorporate them into a continuous microfluidic stream. These techniques may also be extended to assays performed on fluorescence reporting beads as well as cell-based assays.

The localisation of fluorescence on the beads makes detection more difficult. If a fluorescent bead and the excitation laser do not overlap as the droplets passes, there will be no fluorescence, despite the present of the bead. To counter this problem the excitation laser beam is expanded in order to excite the entire droplet. The laser focus is not uniform across the droplet, and hence the signal recorded from the PMT is dependent on where the bead is relative to the laser.

Figure 4:
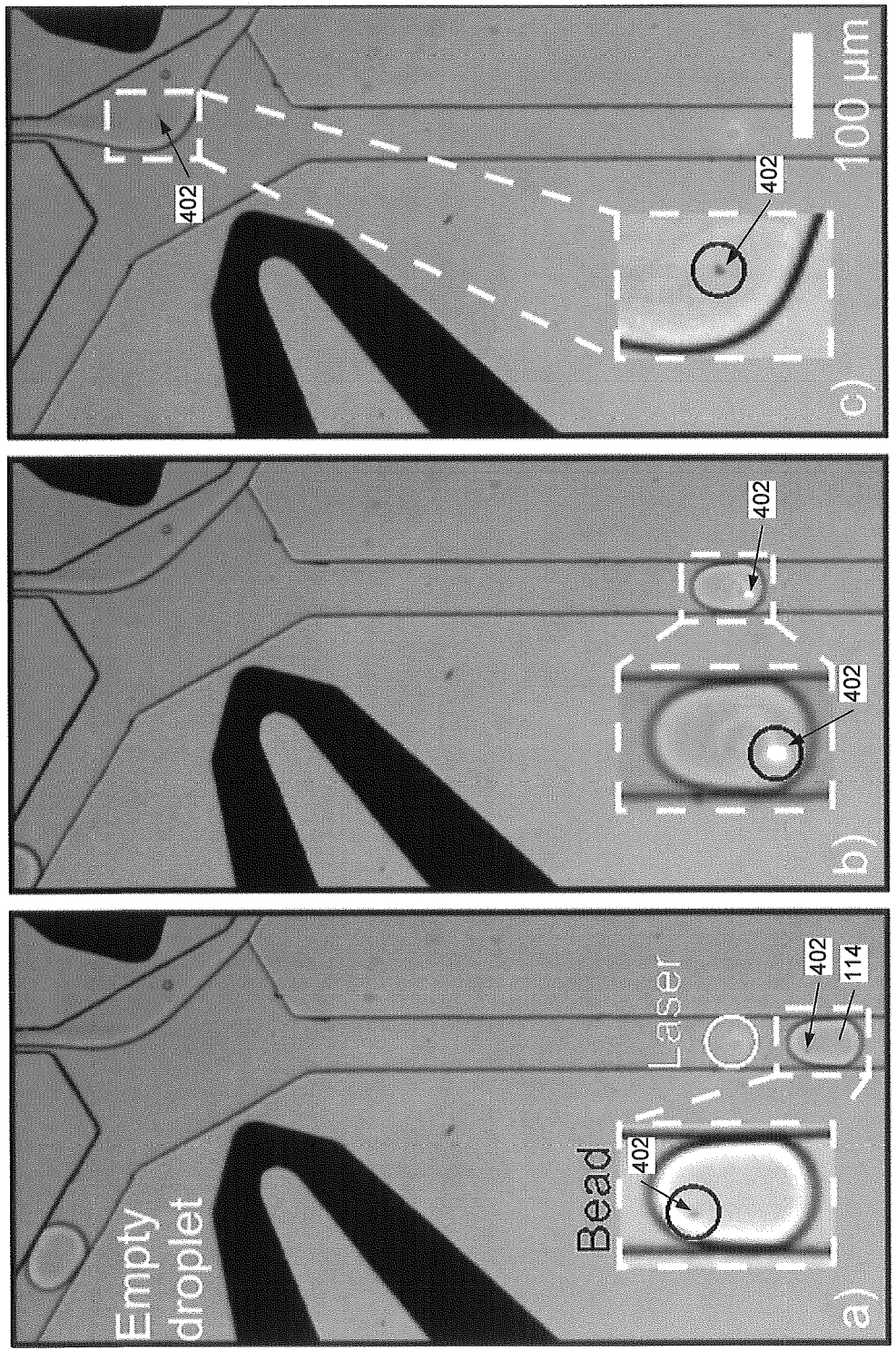
FIGS. 4a to 4c show a sequence of micrographs illustrating the selection of a droplet containing a fluorescent bead.

To study the selection of bead containing droplets, we generated droplets of a solution containing 2 μm diameter fluorescent beads (0.005 volume %) in phosphate buffer. This concentration results in ~$10^4$ beads/μl. With an approximate droplet volume of 50 pl, the number of beads per droplet is ~0.6. This resulted in most of the droplets containing either one or no beads. The fluorescence intensity emitted by the beads was used, as previously, as the signal to trigger a high-voltage pulse. FIG. 4 shows a sequence of micrographs where a droplet containing a fluorescent bead is selected and merged with the lateral stream. The bead can be seen both inside the droplet before fusion (FIGS. 4a, b) and within the stream after fusion (FIG. 4c).

We have described examples of techniques which use an electric field to coalesce a droplet of an emulsion with an aqueous stream. However, the inventors have determined that use of an electric field is not essential, which is helpful because although the above-described techniques perform well at a droplet frequency of 1 Kz, at frequencies of the order of 10 Kz the droplets are so close together that such electric field based techniques can be difficult to employ effectively. In such cases a high throughput screening may be performed in a different, albeit related manner, as selecting droplets of interest in a first, upstream stage to direct only the selected droplets into a microchannel and then coalescing all the droplets in that microchannel with a second, aqueous stream. This is illustrated schematically in FIGS. 5a and 5b which illustrate microfluidic screening apparatus 500 comprising a first, selection stage 502, and a second, droplet merger stage 504. In the first, selection stage 502 a droplet 114 is selectively directed into one of a plurality of microchannels 502a, b, for example by detecting fluorescence and applying an electric field. The skilled person will, however, be aware of many other techniques which may be employed in this stage. Although only two streams are illustrated a large library of items for analysis may be divided into many different streams, either at a single junction or using a tree structure.

These stream of selected droplets, in the illustrated example contained within microchannel 502b are then all merged with an aqueous stream 118, in the illustrated example using a geometric technique in which the microchannel 502b is narrowed to confine a droplet 114 in at least one dimension until the droplet is allowed to expand into a chamber 506 where surface forces bring the droplet towards a more symmetrical (spherical) shape thus de-stabilising interface 120 and causing a droplet 114 to merge with the laminar flow of aqueous stream 118. The skilled person will appreciate that FIG. 5b illustrates one example of a geometry which will cause droplet 114 to merge with stream 118, but the skilled person will appreciate that other geometries are possible.

One important advantage of the above-described techniques is that they facilitate the combination of microdroplets-based techniques with microfluidic analytical devices. In general microfluidic analytical devices will not work satisfactorily with a stream of emulsion as oil affects the operation of such devices. The above described techniques enable the contents of a droplet to be separated from the oil so efficiently that the resulting stream of aqueous solution is as if the materials carried by the solution have never been in an emulsion in the first place. Further, the aqueous stream may be employed to functionally process the contents of a droplet, for example by cleaving a material such as DNA from a solid support such as a microsphere. The skilled person will appreciate that the above techniques may be employed for a very wide variety of chemical and biological procedures including, but not limited to, the processing and analysis of DNA, proteins, cells, enzymes, antigens and the like, in particular, in high-throughput systems, as well for other chemical and/or biological reactions and processes, for example PCR (polymerase chain reaction), and in a wide variety of sensors and detectors, for example for detecting biological, chemical or radiological threats.

In summary we have demonstrated technology capable of extracting the contents of microdroplets on-chip and incorporating them into a continuous microfluidic stream. We are able to select individual droplets based on their contents. As a proof of principle, we have implemented a fluorescence detection system and used it to collect droplets containing low levels of a fluorescent dye as well as single fluorescent beads. This technology enables many applications, for example in the fields of directed evolution, enzyme inhibition studies, high-throughput drug screening, and more. This device has the potential to combine all of the available microfluidic techniques with microdroplet based screening. Moreover, further control can be provided by adjusting the composition of the receptor stream. This stream can be used to quench reactions so that their endpoints are accurately determined, ensure that cells do not encounter any adverse environments or, on the other hand, lyse cells to study their contents on-chip after a reaction carried out in droplets.

In the case of microspheres or microbeads, these may be used to carrier a biological material such as DNA, which may afterwards be cleaved off the solid support in or downstream of the second stream for further processing and/or analysis.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of accessing the contents of a droplet of an emulsion in a microfluidic system, the method comprising:
   flowing the emulsion alongside a continuous. non-emulsive stream of second fluid such that said droplet coalesces with said stream of second fluid; and accessing said contents of said droplet in said second stream.

2. A method as claimed in claim 1 wherein said flowing provides an interface between said emulsion and said stream of second fluid, the method further comprising de-stablising said interface.

3. A method of accessing the contents of a droplet as claimed in claim 1 wherein said flowing provides an interface between said emulsion and said stream of second fluid and comprises flowing said droplet using a geometry which causes said droplet to collide with said interface.

4. A method of accessing the contents of a droplet as claimed in claim 3 wherein said flowing comprises confining a said droplet in a microfluidic channel and allowing a dimension of said confined droplet to expand into a chamber in which said interface is located.

5. A method as claimed in claim 1 wherein said flowing provides an interface between said emulsion and said stream of second fluid, the method further comprising applying one or both of an electric and magnetic field across said interface to alter a trajectory of a said droplet of said emulsion to cause said droplet to coalesce with said stream of second fluid.

6. A method as claimed in claim 1 performed on a microfluidic platform, wherein said second fluid comprises an aqueous fluid, and wherein the method further comprises analysing said contents of said droplet in said second stream on said microfluidic platform.

7. A method as claimed in claim 1 further comprising forming said emulsion using a microfluidic technique.

8. A method as claimed in claim 1 further comprising using a composition of said second fluid to perform a biological or chemical operation on said contents of a said droplet.

9. A method as claimed in claim 1 wherein said contents include at least one insoluble object.

10. A method as claimed in claim 9 wherein, on average, said contents of said droplets include substantially no more than one said insoluble object.

11. A method of accessing the contents of a droplet of an emulsion in a microfluidic system, the method comprising:
    flowing the emulsion alongside a continuous, non-emulsive stream of second fluid to provide an interface between said emulsion and said stream of second fluid; and
    applying one or both of an electric and magnetic field across said interface to alter a trajectory of a said droplet of said emulsion to cause said droplet to coalesce with said stream of second fluid; and
    accessing said contents of said droplet in said second stream.

12. A method as claimed in claim 11 further comprising detecting one or more properties of said droplet and selectively applying said field responsive to said detecting to conditionally transfer said contents of said droplet to said second stream dependent on said one or more properties of said droplet.

13. A method as claimed in claim 12 wherein said contents include a fluorescent material, wherein said one or more properties include fluorescence, and wherein said detecting comprises detecting said fluorescence.

14. A method as claimed in claim 11 wherein said field comprises an electric field and wherein said stream of second fluid comprises an aqueous stream.

15. A method as claimed in claim 14 wherein said flowing emulsion and said stream of second fluid comprise substantially parallel laminar flows and wherein said electric field is substantially perpendicular to said laminar flows.

16. A method as claimed in claim 15 wherein when said electric field is not applied said droplet flows past said interface at a distance of greater than 1 µm from said interface, and wherein said electric field, when applied, has a value at said interface of at least $10^6$ V/m.

17. A method as claimed in claim 11 wherein said field comprises a pulsed electric field applied by a pair of electrodes and wherein, during a duration of a pulse of said field, only a single said droplet is present between said electrodes.

18. A method of microfluidic screening the droplets of a flowing emulsion, the method comprising:
    flowing the emulsion alongside a continuous, non-emulsive stream of a second fluid to provide an interface between said emulsion and said stream of second fluid to cause said droplet to coalesce with said stream of second fluid; and
    detecting a property of said droplets of said flowing emulsion prior to said droplets flowing past said interface; and
    selectively incorporating the contents of said droplets of said flowing emulsion into a continuous microfluidic stream of said second fluid; and
    wherein the method further comprises selectively directing the trajectory of a said droplet responsive to said detecting to thereby selectively coalesce said droplets of said flowing emulsion with said second stream responsive to said detecting.

19. A method as claimed in claim 18 wherein said selective directing comprises selectively directing a said droplet into one of a plurality of microfluidic channel; leading towards a region of coalescence with said second stream, and wherein said flowing to cause said droplet to coalesce in performed downstream of said selecting.

20. A microfluidic apparatus for accessing the contents of a droplet of an emulsion in a microfluidic system, the apparatus comprising:
    a micro-droplet generator to generate the droplet; and
    a flow cell, said flow cell having:
        a first microfluidic entry channel and first microfluidic exit channel for flowing said emulsion through said cell;
        a second microfluidic entry channel and second microfluidic exit channel for flowing a stream of second fluid through said cell, and
    wherein, in operation, an interface is formed in said cell between said emulsion and said stream of second fluid, and
    wherein said apparatus further comprises a system to cause said droplet to coalesce with said stream of second fluid;
    whereby said contents of said droplet in said second stream are accessible from said second stream of fluid from said second microfluidic exit channel.
    wherein said system to cause said droplet to coalesce with said stream of second fluid comprises a pulse generator and a pair of electrodes,
    the microfluidic apparatus further comprising a detector to detect one or more properties of said droplet,
    wherein the pulse generator is configured to be triggered by said detector to generate a field to cause said droplet to coalesce with said stream of second fluid.

21. A microfluidic system comprising:
    a micro-droplet generator to droplets; and
    an emulsion input to receive a stream of emulsion comprising a plurality of said droplets of a dispersed phase of said emulsion in a continuous liquid phase;
    a second input to receive a continuous, non-emulsive stream of second fluid;

a system for selectively merging a droplet into said continuous stream of second fluid responsive to a content of the said droplet: and a microfluidic output to provide said stream of second fluid including the contents of a said droplet to a microfluidic analytical device, wherein said system for selectively merging a droplet comprises a pulse generator, a pair of electrodes and a detector to detect one or more properties of said droplet, the pulse generator configured to be trigger by said detector to generate a field to cause said droplet to coalesce with said stream of second fluid.

22. A microfluidic system as claimed in claim 21 wherein, in operation, said second fluid and said dispersed phase of said emulsion have substantially the same composition, and wherein said second fluid lacks substantially any dispersed component of said continuous phase of said emulsion.

23. A microfluidic system as claimed in claim 21 wherein said system for selectively merging a droplet into said continuous stream of second fluid comprises a system to selectively direct said droplet into one of a plurality of microfluidic channels, and wherein at least one of said microfluidic channels is followed downstream by a region configured to coalesce droplets in said channel with said second stream.

24. A microfluidic system as claimed in claim 21 wherein said system for selectively merging a droplet into said continuous stream of second fluid comprises a system to selectively coalesce droplets in said channel with said second stream by selective application of one or both of an electric and magnetic field.

* * * * *